United States Patent [19]

Nasmyth et al.

[11] Patent Number: 4,925,791

[45] Date of Patent: May 15, 1990

[54] EUCARYOTIC EXPRESSION VECTORS

[75] Inventors: Kim A. Nasmyth; Allan M. Miller, both of Cambridge, England

[73] Assignee: Celltech Limited, Slough, England

[21] Appl. No.: 852,456

[22] PCT Filed: Jul. 22, 1985

[86] PCT No.: PCT/GB85/00325

§ 371 Date: Mar. 18, 1986

§ 102(e) Date: Mar. 18, 1986

[87] PCT Pub. No.: WO86/00926

PCT Pub. Date: Feb. 13, 1986.

[30] Foreign Application Priority Data

Jul. 20, 1984 [GB] United Kingdom ................ 8418511
Sep. 14, 1984 [GB] United Kingdom ................ 8423301
Nov. 21, 1984 [GB] United Kingdom ................ 8429392

[51] Int. Cl.$^5$ .................. C12P 21/00; C12P 21/32; C12N 15/00; C12N 5/00
[52] U.S. Cl. ............... 435/69.1; 435/172.3; 435/255; 435/256; 435/320; 435/172.1; 435/240.2; 935/28; 935/37; 935/56; 935/69; 536/27
[58] Field of Search .............. 435/68, 70, 172.3, 91, 435/255, 320, 172.1, 256, 240.2; 935/37, 28, 69, 56, 70; 536/27

[56] References Cited

U.S. PATENT DOCUMENTS

4,546,082 10/1985 Kurjan et al. ................ 435/172.3
4,588,684 5/1986 Brake et al. ................ 435/68

FOREIGN PATENT DOCUMENTS

123294 10/1984 European Pat. Off. ............. 435/68
123544 10/1984 European Pat. Off. ............. 435/68
85-2200 5/1985 PCT Int'l Appl. .

OTHER PUBLICATIONS

Emr, S. D. et al., *Proceedings of the National Academy of Sciences*, U.S.A., vol. 80, pp. 7080-7084, (1983).
Errede, B. et al., *Mol. Cell Biol.*, vol. 4, pp. 1393 to 1401, (1984).
Hagen, D. C. et al., *J. Mol. Biol.*, vol. 78, pp. 835-852, (1984).
Stern, M. et al., *J. Mol. Biol.*, vol. 178, pp. 853-868, (1984).
Brake, A. J. et al., *Proc. Nat'l. Acad. Sci.*, U.S.A. vol. 81, pp. 4642-4646, (1984).
Miller, A. M. et al., *Nature*, vol. 314, pp. 598-603, (1985).
Wilson, K. L., *Mol. Cell Biol.*, vol. 4, pp. 2420-2427, (1984).
R. E. Jenson, University of Oregon, part of a dissertation, (1983).
Chemical Abstract, 84871z, vol. 101, part 11, p. 145, (1984).
Chemical Abstract, 1318W, vol. 102, part 1, p. 134, (1985).
Guarente et al., vol. 79, pp. 7410-7414, Dec. 1982, "A Gal 10-Cycl Hybrid Yeast Promotor Identifies the Galy Regulatory Region as an Upstream Activation Site".
Herskowitz et al., "The Molecular Biology of the Yeast Saccharomyces", Edited by Strattern, 1981.
Nasmyth, *Ann. Rev. Genet.*, 1982, vol. 16, pp. 441-499, "Molecular Genetics of Yeast Mating Type", 1982.

*Primary Examiner*—Robin Teskin
*Attorney, Agent, or Firm*—Spencer & Frank

[57] ABSTRACT

A eukaryotic expression vector includes a controllable repressor operator sequence witin the expression control sequence of the vector. The controllable repressor operator sequence represses expression of a heterologous structural gene located downstream of the expression control sequence in the presence of a gene product or a combination of gene products of a yeast mating type locus. This allows control of the expression level of the heterologous structural gene. Controllable repressor operator sequences responsive to the a1/α2 and α2 gene products of the MATa and MATα yeast mating type locus alleles are described, both derived from genetic material and synthesized chemically.

56 Claims, 3 Drawing Sheets

EUCARYOTIC EXPRESSION VECTORS

FIELD OF THE INVENTION

This invention relates to the field of recombinant DNA biotechnology. In particular the invention relates to a eukaryotic expression vector, a host organism transformed with the eukaryotic expression vector, specific DNA sequences and to a process for the production of polypeptide.

BACKGROUND TO THE INVENTION

In recent years, advances in biotechnology have made possible the production of desirable polypeptide products by inserting an appropriate heterologous gene into a host organism and subsequently culturing the organism to produce the polypeptide. In broad terms, these techniques involve the insertion of a structural gene coding for the desired polypeptide into a vector capable of stable existence in the cells of a host organism. The gene is inserted into the vector in a position relative to appropriate expression control sequences such that once within the host organism, the vector expresses the inserted gene to produce the polypeptide. Such vectors are referred to in the art as "expression vectors" and have been the subject of considerable research. The main thrust of the research has been to develop expression vectors which are compatible with prokaryotic host organisms such as bacteria (for example, *Escherichia coli* (E. coli)), and eukaryotic host organisms such as yeasts (for example, *Saccharomyces cerevisiae*) and cells of higher organisms (for example mammalian cells in tissue culture). A wide variety of polypeptides have been produced, such as animal and human hormones, enzymes and other useful proteins. The research has involved detailed studies of expression control sequences affecting expression, and in particular, promoter sequences, which are responsible for directing transcription of genetic material.

The commercial use of expression systems is hampered by the lethal or debilitating effect of toxic expression products upon the host organism. It has been recognised therefore that it is desirable to regulate heterologous gene expression. In a regulated expression system, the host organism can be cultured to produce a high cell density whilst expression of a gene in an inserted vector is kept at a low level. When the host organism reaches an appropriate cell density, expression may be induced, for example, by adding a material having a regulating effect on the culture medium. A large number of expression control sequences (including promoters) which allow a degree of expression regulation have been identified both for prokaryotic and eukaryotic host organisms. In published European Patent Application EP-A2-0073635, a yeast expression vector is described which makes use of the control sequences of the yeast phosphoglycerate kinase (PGK) gene and which allows expression level control by adjusting the level of fermentable carbon in the culture medium. Published European patent application EP-A2-0118393 describes a prokaryotic and eukryotic expression system based upon the control sequences of heat-shock genes derived from *Drosophlia melanogaster*. The control sequences include temperature-dependent promoters which allow for expression level control by adjusting the temperature of the culture medium. British patent specification No. 1557774 and published International patent application No. WO 84/01171 describe prokaryotic expression level control systems in which the average number of plasmids in each cell (the copy number) is controlled. Copy number control allows a regulation of the net gene expression occurring in each cell of the host organism.

The known regulated expression systems for eukaryotic host organisms do not have the ability to control expression over a wide range of expression levels. In many cases, it is not possible to reduce the concentration of toxic products, by promoter control alone, to a level at which the cell growth is unaffected and yet to allow for a significant production of the desired polypeptide when required.

The object of the present invention is to provide a eukaryotic expression vector capable of controlling the expression level of a heterologous gene, inserted in a host organism, over a wide range of expression levels.

The molecular biology of common brewers yeast, *Saccharomyces cerevisiae*, has been a target of considerable research effort. In particular the elucidation of the nature and operation of the mating type locus and its operation have been studied in depth. (See for reviews: Nasmyth Ann. Rev. Genet. (1982) 16 439–500 and Klar et al "Microbial Development" (1984) pub. Cold Spring Harbor Laboratory 151–195).

The mating type locus, which is located on chromosome III of the yeast genome, orchestrates the production of gene products necessary for the complex process of yeast mating. There are essentially three phenotypes of naturally occurring yeasts, a type haploids, $\alpha$ type haploids and a $\alpha$ diploids. A haploid can mate with a haploid of complementary phenotype to produce an a/$\alpha$ diploid. a/$\alpha$ diploids do not mate but are capable of sporulation under conditions of nutrient starvation. The mating type of the yeast is determined by a number of expression products of the yeast genome. The products expressed are controlled, in turn, by the expression products of the mating type locus. There are two active alleles of the yeast mating type locus, known as MATa and MAT$\alpha$. Mating type locus allele MATa transcribes the gene known as al and mating type-locus allele MAT$\alpha$ transcribes genes known as $\alpha 1$ and $\alpha 2$. It is the expression of these genes which defines mating type. The a mating type is found where no MAT genes are expressed, the $\alpha$ type requires expression of both $\alpha 1$ and $\alpha 2$, and the a/$\alpha$ diploid requires expression of a1 and $\alpha 2$. The combination of gene expression products from the mating type locus acts on the yeast genome to promote or repress the production of specific gene products for mating.

We have discovered DNA sequences within the yeast genome which act as expression repressor operators when in the presence of mating type locus gene products.

According to the present invention there is provided a eukaryotic expression vector comprising an expression control sequence and a heterologous structural gene located relative to the expression control sequence such that the expression control sequence is capable of directing expression of the heterologous structural gene, characterised in that the expression control sequence includes a controllable repressor operator sequence comprising a DNA sequence which is capable of repressing expression in the presence of a gene product or a combination of gene products of the yeast mating type loci.

The vector of the invention allows control of the expression level of the heterologous structural gene over a wide range, thereby allowing growth of a culture whilst expression of the heterologous structural gene is substantially repressed prior to removing or reducing the level of the yeast mating type locus product or products to allow expression of the heterologous structural gene.

The eukaryotic expression vector of the invention may be an expression vector suitable for use in yeast or, for example, an expression vector suitable for use in a mammalian cell system. A suitable yeast expression vector may, for example, comprise a yeast expression vector such as the PGK promoter-based expression vectors described in European patent application EP-A2-0073635. Alternatively, the expression vector may be a vector suitable for the expression of gene products in a mammalian cell system such as an SV40 or bovine papilloma virus (BPV) expression vector.

The term "expression control sequence" as used herein denotes a sequence of DNA containing the control signals necessary to direct expression of the heterologous structural gene. The expression control sequence includes a promoter, and may include for example one or more upstream activator sequences (UAS) and other functional sequences.

The expression control sequence of the eukaryotic expression vector may comprise any functional eukaryotic promoter. The eukaryotic promoter may comprise a yeast promoter, in particular a yeast promoter which is not normally under mating type control. For instance, the yeast promoter may be a promoter derived from the yeast TRP1 ADH1, URA3+, HIS3+, CYC1 or PGK genes.

The controllable repressor operator sequence is inserted into the expression control sequence in a position where expression of the structural gene may be repressed. More than one copy of the controllable repressor operator sequence may be inserted into the expression control sequence to enhance repression. Preferably, the controllable repressor operator sequence is inserted between an upstream activator sequence (if present) and the "TATA box" of the yeast promoter. The controllable repressor operator sequence may lie upstream of an upstream activator sequence (if present).

The promoter may comprise a promoter suitable for use in an animal cell culture expression system. For example the promoter may comprise a viral promoter such as an SV40 promoter or a mammalian promoter such as a mammalian metallothionein promoter (for example, a mouse metallothionein promoter).

As used herein the term "heterologous structural gene" refers to a gene not naturally found in the host organism in which the expression vector is to be expressed. As used herein the term "polypeptide" denotes any polypeptide and includes hormones (such as growth hormones) and enzymes (such as chymosin).

The term "controllable repressor operator sequence" as used herein denotes an operator comprising a sequence of DNA capable, when inserted into the expression control sequence of a eukaryotic expression vector, of repressing expression in the presence of one or more of the gene products of the yeast mating type locus.

The gene products of the yeast mating type loci may be produced from more than one site in the yeast genome. For example copies of the relevant genes occur at silent mating type loci HMLα and HMRa. Gene products from these loci may be used to effect repression by the controllable repressor operator sequence.

The controllable repressor operator sequence may comprise a DNA sequence which represses expression in the presence of a combination of the a1 and α2 gene products of the MATα and MATa yeast mating type locus alleles. The DNA sequence has been shown to occur repeatedly in those genes specific to haploid yeast types. In a diploid yeast, the a1 and α2 gene products repress expression of haploid specific genes.

In broad terms, a DNA sequence comprises a double-stranded sequence of about twenty base pairs having subsequences of about seven base pairs at opposite ends and in complementary strands of the sequence, wherein the subsequences are substantially inverted repeats each of the other. Preferably the DNA is selected from one of the following sequences

| | |
|---|---|
| CAATGTAGAAAAGTACATCA | (MAT α1) |
| GCTTGTTAATTTACACATCA | (STE5(−196)) |
| TCATGTACTTTTCTGCATCA | (STE5(−179)) |
| CCGCGTTAAAACCTACATCA | (HO −1752) |
| TTATGTTAAAAGTTACATCC | (HO −1391) |
| GCCTGCGATGAGATACATCA | (HO −1328) |
| TAGAGTGAAAAAGCACATCG | (HO −1208) |
| TCATGTATTCATTCACATCA | (HO −736) |
| ACATGTCTTCAACTGCATCA | (HO −669) |
| TCGTGTATTTACTTACATCA | (HO −576) |
| TCATGTTATTATTTACATCA | (HO −411) |
| TCATGTCCACATTAACATCA | (HO −371) and |
| GCGTTTAGAACGCTTCATCA | (HO −150) | wherein (using the standard notation for nucleotide bases employed throughout this specification) A denotes adenine, T denotes thymine, G denotes guanine and C denotes cytosine. (The source of the sequence and the position of the sequence within the gene are shown in parenthesis. It will be understood that the sequences shown above represent a single strand of a double stranded portion of DNA, the strand not shown being complementary to the shown strand.).

The prevalence of the DNA sequence in haploid specific genes allows for the establishment of a statistical consensus sequence which provides a statistical best fit of the individual sequences. The controllable repressor operator sequence may comprise a DNA sequence having substantially the following nucleotide base sequence:

TC(A or G)TGTNN(A or T)NANNTACATCA wherein N denotes a nucleotide base selected from adenine, thymine, guanine and cytosine.

Alternatively, the controllable repressor operator sequence may comprise a DNA sequence which represses expression in the presence of the α2 gene product of the MATα yeast mating type locus allele. The DNA sequence has been shown to occur repeatedly in those genes specific to a haploid yeast types. In α yeast cells, genes essential for a mating are repressed by the α2 gene product.

In broad terms, such a DNA sequence comprises a double-stranded sequence of about thirty-three base pairs having subsequences of about ten base pairs at opposite ends and in complementary strands of the sequence, wherein the subsequences are substantially inverted repeats each of the other. Preferably the DNA sequence is selected from one of the following sequences:

|   | GTGTGTAATTACCCAAAAAGGAAATTTACATGT | (MFA1) |
|---|---|---|
|   | GCATGTAATTACCGTAAAAGGAAAT-TACATGG | (BAR1) |
| and | TCATGTACTTACCCAATTAGGAAATTTACATGG | (STE2) |

(The source of the gene is shown in parenthesis. It will be understood that the sequences shown above represent a single strand of a double stranded portion of DNA, the strand not shown being complementary to the shown strand.).

The DNA sequence of the α2 product-controllable repressor operator sequence occurs more than once in the yeast genome and, again, it is possible to assign a consensus sequence. The controllable repressor operator sequence may comprise a DNA sequence having substantially the following nucleotide base sequence:

GCATGTAATTACCCAAAAAGGAAATT-
TACATGG

The DNA sequence of the controllable repressor operator sequence may comprise the whole or an operative part of any of the sequences mentioned above, or a functional equivalent thereof.

The sequence may be obtained from natural or mutant yeast genes which are under mating type control, for instance by appropriate restriction enzyme digestion. Preferably, however, the sequence is prepared by chemical synthesis and, where appropriate, ligation of two or more synthetic oligonucleotides.

In a second aspect of the invention we provide a controllable repressor operator sequence capable, when inserted into the expression control sequence of a eukaryotic expression vector, of repressing expression in the presence of a combination of the a1 and α2 gene products of the MATa and MATα yeast mating type allele.

In a third aspect of the invention we provide a controllable repressor operator sequence capable, when inserted into the expression control sequence of a eukaryotic expression vector, of repressing expression in the presence of the α2 gene product of the MATα yeast mating type locus.

The sequences of the second and third aspects of the invention may each be provided with a linker at each end to facilitate the insertion of the sequence into a suitable site in the expression control sequence of a eukaryotic expression vector.

The vectors of the first aspect of the invention may be used to transform or transfect eukaryotic host organisms, for example, by methods well known in the art. The eukaryotic host organism may be a yeast, such as *Saccharomyces cerevisiae* or a higher eukaryotic host organism such as a culture of animal cells.

In a fourth aspect of the invention we provide a eukaryotic host organism transformed with an expression vector according to the first aspect of the invention.

Preferably the host organism is transformed with a eukaryotic expression vector according to the first aspect of the invention and further comprises means for providing a controllable supply of either a combination of the α2 and a1 protein or the α2 protein alone to cause repression of transcription.

The host organism may be transformed with a eukaryotic expression vector according to the present invention and a second vector, allowing the controllable production of either a combination of the a1 and α2 gene products or the α2 gene product alone. The second vector may, for example, comprise a vector capable of producing a controllable level of either a combination of the a1 and α2 gene products or of the α2 gene product alone. A suitable such vector is a temperature-dependent mutant including a MAT gene or, for example, a temperature-sensitive mutant of a SIR gene. A SIR gene regulates mating type gene expression from silent mating type loci HMLα and HMRa. These may be used to provide a regulated supply of the controlling protein or proteins.

Alternatively the yeast strain used as host for the eukaryotic expression vector of the invention may, for example, carry a temperature sensitive mutation in the a1 and/or α2 repressor gene. Thus if transformed cells are grown at a permissive temperature the a1 and/or α2 proteins are functional and repress transcription of the heterologous structural gene, whereas at a restrictive temperature the repressor proteins are inactive, transcription of the heterologous structural gene is not repressed and the heterologous gene product is expressed.

The vector of the present invention and/or the said second vector may be present within the transformed eukaryotic host cells in an episomal form or may be incorporated into the chromosome of the host organism.

Alternatively, the combination of the a1 and α2 gene products or the α2 gene product alone may be introduced into the culture medium from an external source or may be produced in controllable manner on a suitable modified expression vector of the present invention.

In a fifth aspect of the invention we provide a method for preparing a polypeptide comprising culturing a eukaryotic host organism transformed with a vector according to the invention in the presence of one or more gene products of the yeast mating type locus capable of repressing expression of the heterologous structural gene, until a predetermined cell density has been established, and subsequently reducing the level of the gene product or products of the yeast mating locus, thereby allowing expression of the heterologous structural gene and production of the polypeptide.

In a sixth aspect of the invention we provide a eukaryotic expression vector of the present invention in which a restriction site suitable for the insertion of a heterologous structural gene exists in place of the heterologous structural gene. Preferably the restriction site is unique in the vector. A gene coding for a desired polypeptide may readily be ligated into such an expression vector to produce a vector according to the first aspect of the invention.

DETAILED DESCRIPTION OF EMBODIMENTS

EXAMPLE 1

A1 and 2 Controllable Repressor Operator Sequence

Two defined sequences of about forty base pairs, containing receptors for a combination of the a1 and α2 mating type locus gene products were obtained from the promoter of the yeast homothallism (HO) gene. (see Jensen et al Proc. Natl. Acad. Sci. USA (1983) 80 3035–3039)

The first sequence (hereinafter referred to as "Insert A") was obtained by digesting a plasmid containing the yeast HO gene with BamHI and BglII in buffer containing 10 mM Tris.HCl pH 7.4, 10 mM $MgCl_2$, 60 mM NaCl and 2 mM dithiothreitol at 37° C. (Nasmyth—in press). The second sequence (hereinafter referred to as "Insert B") was obtained by digesting a XhoI-linker mutant plasmid, H204 (Nasmyth—in press) with XhoI and NruI in buffer containing 6 mM Tris.HCl pH 7.4, 10 mM $MgCl_2$, 100 mM NaCl and 2 mM dithiothreitol, at 37° C.

Figure 1:
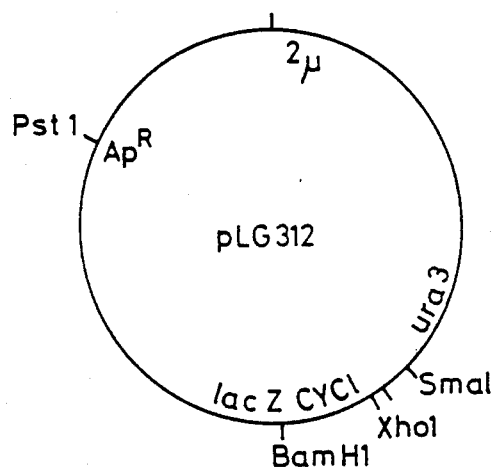
FIG. 1 is a map of plasmid pLG312, a CYC1 lacZ expression vector.

The expression plasmid used in this experiment was that designated pLG312 (Guarente and Mason Cell (1983) 32 1279, and a map of the plasmid is shown in FIG. 1. This plasmid contains a bacterial β-galactosidase structural gene under the transcriptional control of the CYC1 promoter, and a unique XhoI restriction site between the CYC1 upstream activator (UAS) and the promoter TATA box. (The plasmid is also known by an alternative designation: pLG-Δ2925).

Insert A DNA was incubated with T4 DNA polymerase and all four deoxynucleotide triphosphates to generate a blunt ended molecule (Maniatis, Fritsch and Sambrook "Molecular Cloning, A Laboratory Manual" pub. Cold Spring Harbor Laboratory (1982)). This was ligated into XhoI cut blunt ended pLG312. All ligations were with T4 DNA ligase, in buffer containing 66 mM Tris. HCl pH 7.8, 10 mM $MgCl_2$, 20 mM dithiothreitol, and 1 mM ATP. DNA concentrations were 10–15 μg/ml.

Ligation mixtures were transformed into E. coli and ampicillin resistant transformants selected. Recombinant plasmids were identified by colony hybridisation, using a gel-purified fragment of each insert as a probe (Grunstein et al, Proc. Natl. Acad. Sci. USA (1975) 72 3961). Positive clones were analysed further by sub-cloning and sequencing (Sanger et al, Proc. Natl. Acad. Sci. USA (1977) 74 5463). Plasmid pLG312 and analogues of the plasmid carrying insert A or insert B wee used to transform yeast strain M30 (HMLa MATα HMRa sir3$^{ts}$ura3 [ho::TRP1 ade2-1 can1-100 his3 leu2 trp1] to URA+ phenotype.

Four independent transformants were struck out onto β-galactosidase indicator plates. The indicator plates were made as follows.

8.7 g Yeast Nitrogen Base without amino acids
60 mg Adenine sulphate
60 mg Tyrosine
12 g Casamino acids, vitamin assay
24 g Agar made up to 1 liter with water, and autoclaved.
Then
5 ml 1% (w/v) Tryptophan
100 ml 20% (w/v) Raffinose
100 ml 10×M9 (40 g $Na_2HOP_4$, 30 g $KH_2PO_4$, 5 g NaCl, and 10 g $NH_4Cl$ per liter, pH=7)
were added before pouring.

Immediately before use 0.25 ml of (20 mg/ml 5-bromo-4-chloro-3-indolyl-β-D-galactopyranoside in dimethylformamide) was spread on each plate.

Figure 2:
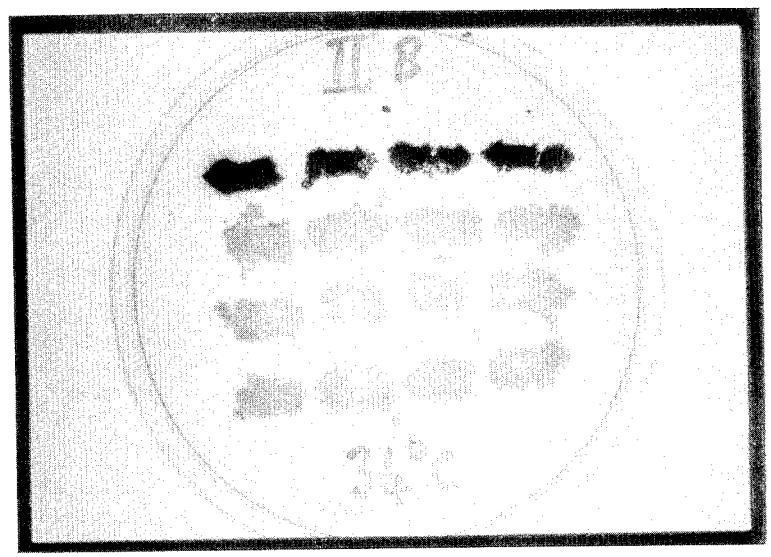
FIG. 2 is a photograph of a β-galactosidase indicator culture plate at 34° C. showing cultures of plasmid PLG312 alone, and with various inserted sequences, transformed into yeast strain M30.
Figure 3:
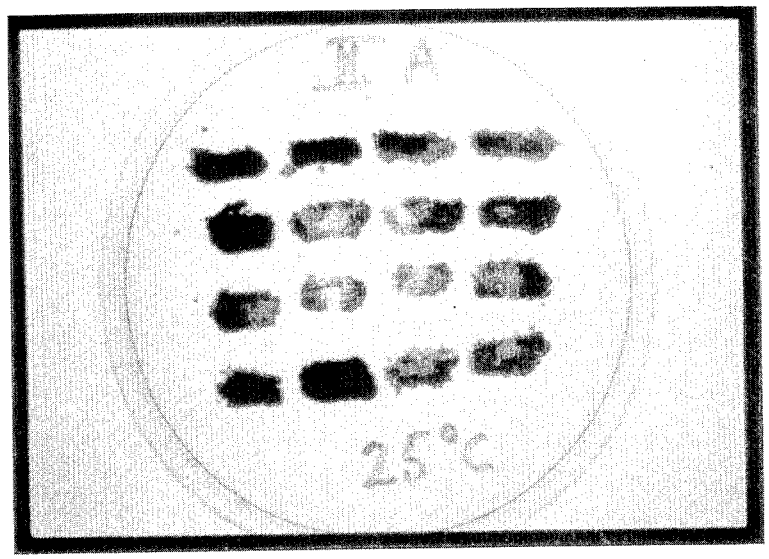
FIG. 3 is a photograph of a similar experiment to that shown in FIG. 1 at 25° C.

The plates were incubated at 20° C. or 34° C. for 4 to 5 days and then photographed. FIGS. 2 and 3 show yeast strain M30 containing various plasmids. Dark colonies signify β-galactosidase production and hence gene expression from the promoters. In each photograph, the top row is yeast transformed with plasmid pLG312, the second row is yeast transformed with plasmid pLG312 including Insert A and the lower two rows are yeasts transformed with plasmid pLG312 including Insert B. The results show clearly repression control of expression of β-galactosidase. The temperature dependent SIR gene in yeast strain M30 causes expression of the mating locus a1 transcript from the HMLa and HMRa silent copy genes, at elevated temperature only. Thus as shown in the Figures the presence of the a1 and α2 gene products has a marked effect upon the expression level of the plasmids including either Insert A or Insert B.

The sequences of the three plasmid constructs used in this experiment, in the region of the XhoI site were as follows:

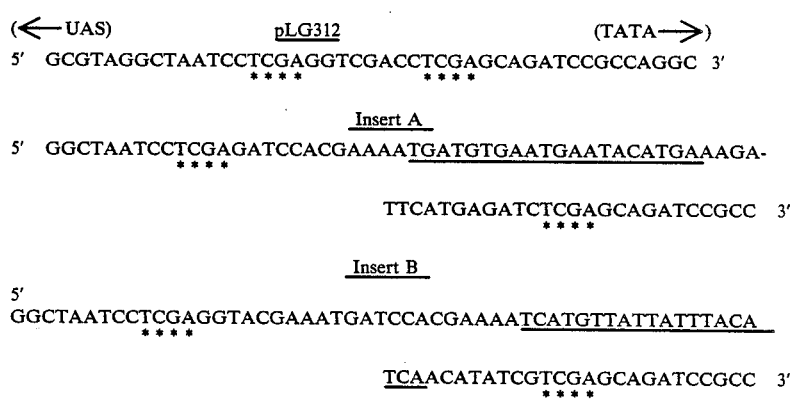

(Asterisks show the XhoI site ends and the underlined part of the sequence indicates the a1/α2 repressor operator).

Table 1 shows the level of β-galactosidase produced by these constructs in an a/α diploid host and in an isogenic a/α diploid host (the latter does not express the a1 gene) both for raffinose and glucose as a carbon source.

β-galactosidase assays were performed using the technique of Miller (Miller J. H. "Experiments in Molecular Genetics" CSH press, N.Y. (1972). Cells were collected by centrifugation, resuspended in Z buffer and permeabilised with $CHCl_3$/SDS. After the reaction was stopped with base, cell debris was removed by centrifugation prior to measuring the $O.D._{420}$. Units were measured as $1000 \times OD_{420}/(OD_{660} \times time$ (in mins)).

The MATα strain used was 822: HMLa MAT HMRa ade2 can1-100 his4 leu2 trp1-1 ura3; this was mated with either W303-1A: (HMIα MATa HMRa ade2-1 can1-100 his3-11,15 leu2-3 trp1-1 ura3) or RS3; (HMIα mat::LEU2 hmr::TRP1 ade2-1 can1-100 his3-11,15 leu2-3 trp1-1 ura3.) The mat::LEU2 construction is described in Miller A. M. et al CSH Symp. Quant. Biol. 49 (in press). These were transplaced into the yeast chromosome (Rothstein R. J. Methods in Enzymology, 101 202 (1983)).

The constructs are under the same carbon source dependence as the parent plasmid, demonstrating the β-galactosidase production is being driven by the CYC1 promoter and is repressed by the inserted sequence.

TABLE 1

| CONSTRUCT | β-GALACTOSIDASE ACTIVITY | | | |
|---|---|---|---|---|
| | Raffinose | | Glucose | |
| | a/α | a⁻/α | a/α | a⁻/α |
| pLG312 | 108 | 91 | 32 | 45 |
| pLG312 + insert A | 2.4 | 91 | 1.1 | 34 |
| pLG312 + insert | 0.67 | 34 | 0.35 | 24 |

EXAMPLE 2

α2 Controllable Repressor Operator Sequence

In a similar experiment to that described in Example 1, a ninety-seven base pair fragment of the yeast STE2 gene, including an operator for the α2 mating type locus gene product was isolated from a plasmid carrying the STE2 gene (plasmid pZV37). (see MacKay, V. L. Methods in Enzymology (1983) 101 325–343 for details of cloning STE genes). The plasmid was digested with HindIII and AvaII and blunt end ligated, in both orientations, into plasmid pLG312. Recombinants were identified and sequenced as before.

The sequences of the two plasmid constructs used in this experiment, in the region of XhoI site were as follows:

```
            GGCTAATCCTCGAGACCTGTGCCTGGCAAGTCGCAGATTGAAG-
                    * * * *
Insert C  TTTTTTCAACCATGTAAATTTCCTAATTGGGTAAGTACATGA-
          TGAAACACATATGAAGAAAAAGCTTCGAGCAGATCCGC
                                      * * * *

GGCTAATCCTCGAAGCTTTTTTCTTCATATGTGTTTCA-
                    * * * *
Insert C' TCATGTACTTACCCAATTAGGAAATTTACATGGTTGAAAAAACTT-
          CAATCTGCGACTTGCCAGGCACAGGTCTCGAGCAGATCCGC
                                         * * * *
```

(Asterisks show the XhoI site ends, and the underlined part of the sequence indicates the α2 repressor operator sequence).

Table 2 shows the level of β-galactosidase produced by these constructs in an α1⁻ cell and in an isogenic α1⁻α2⁻ cell, both for raffinose and for glucose as carbon source. (The latter does not express the α2 gene). The constructs are under the same carbon source dependance as the parent plasmid demonstrating the β-galactosidase production is being driven by the CYC1 promoter and is represented by the inserted sequence.

β-galactosidase assays were performed as in Table 1. The strains used were RS3: (Table 1, which is α1⁻α2⁻) and M48: (HMIα MATα2 matα1::LEU2 hmr:TRP1 ade2-1 can1-100 his3-11,15 leu2-3 trp1-1 ura3)

TABLE 2

| CONSTRUCT | β-GALACTOSIDASE ACTIVITY | | | |
|---|---|---|---|---|
| | Raffinose | | Glucose | |
| | α1⁻ | α1⁻α2⁻ | α1⁻ | α1α2⁻ |
| pLG312 | 44 | 81 | 36 | 49 |
| pLG312 + Insert C | 0.7 | 110 | 0.6 | 62 |
| pLG312 + Insert C' | 0.8 | 110 | 1.0 | 52 |

EXAMPLE 3

Synthesis of a1/α2 Controllable Repressor Sequence

An example of an a1/α2 controllable repressor operator sequence was prepared by oligonucleotide synthesis using the phosphotriester method (see "Oligonucleotide Synthesis" pp. 83–116 Ed. N. J. Gait, IRL PRESS, Oxford (1984)) on a Biosearch SAM ONE oligonucleotide synthesis machine. The oligonucleotide: 5' TCGATTCATGTTATTATTTACATCAT 3' (hereinafter "N1") comprises the native a1/α2 control sequence found upstream of the HO gene (HO-411), plus an additional sequence of five nucleotides (5' TCGAT 3') to allow ligation into a XhoI or SalI restriction site. A mixture of oligonucleotides each of which are essentially complementary to oligonucleotide N1 was prepared by mixed synthesis. These oligonucleotides are represented as: 5' TCGAATGATX-TAAATAATAACATGAA 3', where X denotes A or C or T (hereinafter "N2", "N3" and "N4" respectively). The oligonucleotides were purified on a 20% polyacrylamide gel in TBE buffer (0.089M Tris-borate, 0.089M boric acid and 0.002M EDTA) containing 2 ug/ml ethidium bromide. The DNA was visualised using an ultra violet (UV) light and the highest molecular weight band from each synthesis was cut from the gel, dialysed into water and vacuum dessicated. The final material was redissolved in water. When annealed together using standard techniques oligonucleotides N1 and N2 to N4 generated duplex DNA with 5' TCGA 3' single stranded overhangs, as follows:

5' TCGATTCATGTTATTATTTACATCAT 3' N1

3' AAGTACAATAATAAATXTAGTAAGCT 5' N2-4 where X = A, C, or T

Two further examples of a1/α2 controllable repressor operator sequences were prepared using an automated DNA synthesiser (Patel, Millican, Bose, Titmas, Mock and Eaton (1982) Nucl. Acids. Res. 10 6505).

The first example (designated oligonucleotide "N5" and complementary oligonucleotide "N6") comprised the native a1/α2 repressor operator sequence found upstream of the HO gene (HO-411) substantially as described above, but differed from the above example, in that the additional sequence of 5' nucleotides was 5' TCGAG 3' for oligonucleotide N5 and 5' TCGA 3' for the complementary oligonucleotide N6. In addition, oligonucleotide N6 was not prepared in a mixed synthesis. The oligonucleotides synthesised were: 5'TCGAGTCATGTTATTATTTACATCA 3' (N5) and 5' TCGATGATGTAAATAATAACATGAC 3' (N6). When annealed together using standard techniques, these oligonucleotides generated duplex DNA with 5' TCGA 3' single stranded overhangs, as follows:

5' TCGAGTCATGTTATTATTTACATCA 3' N5

3' CAGTACAATAATAAATGTAGTAGCT 5' N6

The second example (designated oligonucleotide "N7" and complementary oligonucleotide "N8") was that of a consensus sequence i.e. a sequence which has not been found to occur naturally as an a1/α2 repressor operator sequence, but which is predicted to function as an a1/α2 control sequence. The two oligonucleotides, synthesised using an automated DNA synthesiser (Patel, Millican, Bose, Titmas, Mock and Eaton (1982) Nucl. Acids. Res. 10 5605), were: 5' TCGAGTCGTGTTATTATTTACATCA 3' (N7) and 5' TCGATGATGTAAATAATAACACGAC 3' (N8). The sequence formed by these two oligonucleotides differs from the HO-411 control sequence by a single base substitution (A to G) at position 3 of the control sequence. When annealed together using standard techniques oligonucleotides N7 and N8 generated duplex DNA with 5' TCGA 3' single stranded overhangs as follows

5' TCGAGTCGTGTTATTATTTACATCA 3' N7

3' CAGCACAATAATAAATGTAGTAGCT 5' N8

EXAMPLE 4

Synthesis of α2 Controllable Repressor Sequence

The α2 controllable repressor sequence found in the 5' region of the MFAI gene (Miller, MacKay and Nasmyth Nature (1985) 314 589), was synthesised chemically (Patel, Millican, Bose, Titmas, Mock and Eaton Nucl. Acids. Res. (1982) 10 5605). Four oligonucleotides were prepared to construct the 33 base pair sequence, these were: 5' TCCTTTTTGGGTAATTACACAC 3' (N9), 5' TCGAACATGTAAATT 3' (N10), 5' AAGGAAATTTACATGT 3' (N11), 5' TCGAGTGTGTAATTACCCAAA 3' (N12). When annealed together, these oligonucleotides generated duplex DNA with 5' TCGA 3' single stranded overhangs, as follows:

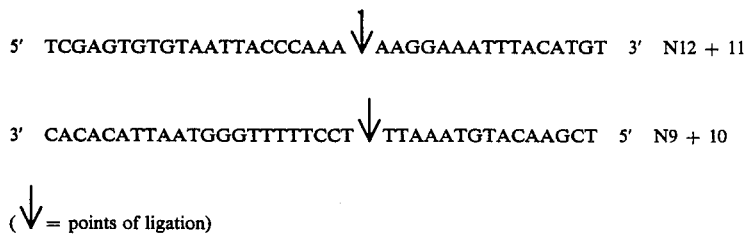

(⇓ = points of ligation)

EXAMPLE 5

Construction of CYCl Yeast Promoter with a1/α2 Controllable Repressor Sequences

The synthetic oligonucleotides which define a1/α2 controllable repressor sequences described in the first part of Example 3 were inserted into pLG312 (Guarente and Mason Cell (1983) 32 1279) to test the in vivo effect of these sequences on a heterologous (CYCl) promoter.

Oligonucleotide N1 and the mixed synthesis oligonucleotides N2-4 were treated with polynucleotide kinase to generate 5' phosphate groups. 45 pg of the purified oligonucleotides from each synthesis were mixed, 10 μCi gamma (α) $^{32}$p ATP (specific activity 3000 Ci/m-mole) was added, and the volume was increased to 30 μl by the addition of kinase buffer (66 mM Tris.HCl pH 8, 10 mM MgCl₂ 10 mM dithiothreitol). 5 units of polynucleotide kinase were added and the mixture incubated at 37° C. for 5 minutes. An additional 30 nmole of unlabelled ATP was then added and the incubation was continued for a further 55 minutes. Following the kinase reaction, the oligonucleotides were annealed by placing the reaction tube in a crystallising dish containing water at 75° C., and allowing the mixture to cool over a period of 30 minutes. The annealed oligonucleotides were then cooled to 4° C. This produced a heteroduplex with a 5' TCGA single stranded overhang at each end. Yeast plasmid vector pLG312 DNA (2 μg) was digested with SalI (5 units) at 37° C. for 1 hour in buffer containing 6 mM Tris. HCl pH 7.9, 6 mM MgCl₂ 150 mM NaCl, 5 mM dithiothreitol. The SalI enzyme was inactivated by heating to 68° C. for 10 minutes following the reaction. The annealed oligonucleotides were ligated into he SalI cut pLG312 DNA in DNA ligase buffer (50 mM Tris HCl pH 7.8, 10 mM MgCl₂, 20 mM dithiothreitol, 1 mM ATP) containing 5 units of DNA ligase and final concentrations of 12.5 μg/ml vector DNA and 0.3 μg/ml annealed oligonucleotide. Incubation was at 15° C. for 15 hours. DNA ligase was inactivated by heating at 68° C. for 10 minutes following the reaction, and the ligated DNA redigested with SalI enzyme to eliminate recircularised vector molecules.

DNA from the redigested ligated mixture was transformed into E.coli and ampicillin resistant transformants were selected. Plasmid DNA was prepared (Ish-Horowitz and Burke Nucl. Acids. Res. (1981) 9 2989) and analysed by polyacrylamide gel electrophoresis in 7M Urea (Maniatis, Fritsch and Sambrook, "Molecular Cloning" Cold Spring Harbor Laboratory (1982)). The plasmid DNA (1 μg) was cut with XhoI in digestion buffer (6 mM Tris. HCl pH 7.9, 6 mM MgCl2, 150 mM NaCl, 5 mM dithiothreitol), by the addition of 2 units of enzyme followed by incubation at 37° C. The digested DNA was radioactively labelled using DNA polymerase I Klenow fragment (Maniatis, Fritsch and Sambrook, "Molecular Cloning" Cold Spring Harbor Laboratory (1983)). The XhoI-cleaved DNA fragments were sized by autoradiography of a 7M urea polyacrylamide gel, which demonstrated that approximately 50% of the transformants carried a single insertion of the repressor operator sequence.

In order to determine the sequence of the inserted repressor operator sequence, the small XhoI fragments were subcloned into the SalI-cut M13 mp 10 vector using the ligation conditions described above. The M13 mp 10 clones were sequenced by the dideoxy method (Sanger, Nicklen and Coulson Proc. Natl. Acad. Sci USA (1977) 74 5463). This sequence does not reveal the orientation of the inserted sequence with respect to the pLG312 plasmid. The orientation was determined by taking advantage of the Hin fl site at one end of the oligonucleotide inserts. The insert containing pLG312 plasmids were digested with BamHI (which cuts at a unique site about 250 bp away from the insert) in buffer containing 6 mM Tris. HCl pH 7.9, 6 mM MgCl2, 150 mM NaCl, 1 μg plasmid DNA and 2 units of enzyme. Incubation was at 37° C. for 1 hour. The BamHI-cut DNA was radioactively labelled with alpha ($\alpha$) $^{32}P$ labelled deoxynucleotide triphosphates by incubation with DNA polymerase I Klenow fragment (Maniatis, Fritsch and Sambrook "Molecular Cloning" Cold Spring Harbor Laboratory (1982)), and then digested with HinfI (5 units) in buffer containing 6 mM Tris. HCl pM 7.4, 6 mM MgCl2 6 mM 2-mercaptoethanol and 50 mM NaCl. The digested DNA was then analysed by polyacrylamide gel electrophoresis in TBE buffer. The sizes of the labelled DNA fragments produced were compared with the size of the SalI and BamHI fragment of the parent molecule, pLG312. In this way the sequence and the orientation of the cloned oligonucleotides was determined.

Derivatives of the plasmid pLG312 containing the oligonucleotide pairs N5 and N6, and N7 and N8 were also constructed, by the methods described above. The orientation of insertion was determined by digesting the plasmids with XhoI and PvuI enzymes, and analysis of the digests by 0.7% agarose gel electrophoresis (Maniatis, Fritsch and Sambrook, "Molecular Cloning" Cold Spring Harbor Laboratory (1982)), and Southern transfer followed by hybridisation using one of the oligonucleotides as a probe (Southern E. J. Mol. Biol. (1975) 98 503). Insertion of the oligonucleotides at a XhoI site destroys one of the XhoI sites at the junction between plasmid DNA and oligonuclotide, whilst the other site is retained. Southern analysis of the XhoI-PvuI digests determines the orientation of the inserts on the basis of which DNA fragment hybridizes with the oligonucleotide probe.

EXAMPLE 6

Construction of a CYC1 Yeast Promoter with an α2 Controllable Repressor Sequence The methods used to construct a CYC1 promoter with an α2 controllable sequence were broadly the same as those described in Example 5 above. Oligonucleotides N9, N10, N11 and N12 were treated with polynucleotide kinase and annealed to generate a duplex DNA comprising a 33 base pair repressor sequence, and single stranded 5' overhangs for insertion at a SalI or XhoI site. Plasmid pLG312 (1 ug) was digested with XhoI (5 units) for 30 minutes at 37° C. in XhoI digestion buffer (see (Example 5). To the digestion mixture was added 10 units of calf intestinal alkaline phosphatase and incubation continued for a further hour. The reaction was stopped by the addition of an equal volume of buffer-saturated-phenol, followed by an equal volume of chloroform. The aqueous layer was removed and the DNA precipitated by the addition of two volumes of ethanol. After cooling for ten minutes in dry ice-ethanol, the mixture was centrifuged in an Eppendorf centrifuge for five minutes. The supernatant was removed, the precipitate air dried and resuspended in 50 μl of 10 mM Tris.HCl pH 7 1 mM EDTA (TE) buffer.

The annealed oligonucleotides (0.3 μg/ml) and the phosphatase treated vector DNA (12.5 μg/ml) were ligated together as described in Example 5 and the ligation mixture used to transform E. coli. Ampicillin transformants were obtained, and plasmid DNA prepared from these (Ish, Horowitz and Burke Nucl. Acids. Res. (1981) 9). The orientation of oligonucleotide inserts was determined by restriction analysis and Southern hybridization as described in Example 5.

EXAMPLE 7

DEMONSTRATION THAT A CHEMICALLY SYNTHESISED REPRESSOR SEQUENCE CONTROLS THE ACTIVITY OF THE CYC1 PROMOTER IN YEAST

Example 1 demonstrated that DNA fragments carrying an a1/α2 repressor sequence can control a heterologous promoter, namely the CYC1 promoter of yeast. To demonstrate that the chemically synthesised 20 base pair repressor sequence found in the 5' region of the HO gene (HO-411) is sufficient to elicit this control in yeast, the pLG312 derivatives constructed as described in Example 5, were analysed for CYC1 promoter function by assaying β-galactosidase activity as described in Example 1. Two derivatives of plasmid pLG312, one with the repressor sequence inserted in one orientation (insert D), and one with it inserted in the opposite orientation (insert D') were each transformed into yeast strain M30 (sir$^{ts}$) as described in Example 1. A control transformation with pLG312 itself was also performed.

The sequences of the three plasmid constructs used in this experiment, in the region of the XhoI site were as follows:

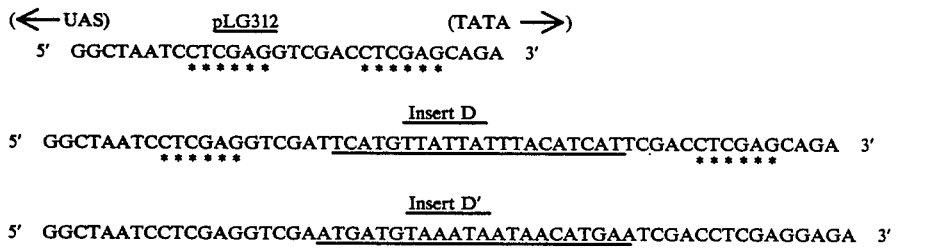

(Xhol sites are marked with asterisks and the inserted sequences are underlined.)

The levels of β-galactosidase activity produced at both 34° C. and 23° C. were measured as described in Example 1. At 34° C. a1 and α2 repressor proteins are synthesised in strain M30, and should recognise the control sequence, thereby repressing transcription. At 23° C. a1 repressor protein should not be produced, hence transcription should be subject to normal CYC1 control. When raffinose was used as the carbon source for M30 carrying pLG312 with either insert D or D', less than 0.5 units of β-galactosidase activity were detected during growth at 34° C., whilst 80 units of activity were detected during growth at 23° C. The induced levels observed were similar to those detected with the parent vector. This demonstrated that the chemically synthesised repressor sequence encoded sufficient information to confer a1/α2-dependent control on a heterologous promoter, and that no other sequences were required.

EXAMPLE 8

INSERTION OF THE a1/α2 REPRESSOR SEQUENCE UPSTREAM OF THE UAS

Example 1 demonstrated the ability of an a1/α2 repressor sequence to control CYC1 promoter activity when inserted between the UAS and TATA box of this promoter. In this example, the effect of inserting insert A upstream of the UAS is described. Insert A was isolated as described in Example 1 as a BglII to BAM HI DNA fragment. The 5' single stranded overhangs were filled in by incubating 1ug of DNA fragment with T4 DNA polymerase (5 units) in 33 mM Tris-acetate pH 7.9, 66 mM potassium acetate, 10 mM magnesium acetate and 0.5 mM dithiothreitol at 30° C. for 30 minutes. Plasmid pLG312 (1 μg) was digested with SmaI (2 units) in buffer containing 6 mM Tris.HCl pH 8, 6 mM MgCl$_2$, 6 mM mercaptoethanol and 20 mM KCl at 37° C. for 1 hour. The enzyme was inactivated by heating at 68° C. for 10 minutes.

Blunt ended insert A was ligated to SmaI digested pLG312 under standard DNA ligase conditions (as previously described), and the mixture used to transform E. coli. A control transformation with pLG312 was also performed. Ampicillin resistant transformants were selected and recombinant plasmids detected by colony hybridisation (as described hereinbefore).

The sequence of the plasmid constructs used in this experiment, in the region of the SmaI site were as follows:

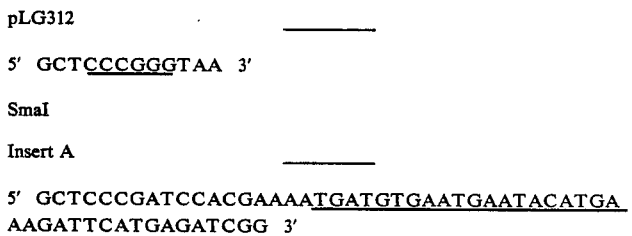

Insertion of insert A at the SmaI site places the a1/α2 control sequences 30–50 base pairs upstream from the beginning of the UAS (see Guarente and Mason (1983), Cell 32 1279). In this position the repressor sequence exerts partial repression on the promoter. Transcription was reduced by about 4- to 7-fold in yeast cells expressing both a1 and α2 proteins, as compared to about 200 fold when insertion was at the XhoI site.

Transcription quantitation was by the protection of radiolabelled DNA from digestion with S1 nuclease (Miller and Nasmyth Nature 312 (1984) 247–51).

EXAMPLE 9

CONSTRUCTION OF A YEAST EXPRESSION VECTOR WITH A PGK PROMOTER AND a1/α2 CONTROLLABLE REPRESSOR SEQUENCE

The a1/α2 controllable repressor sequence was inserted into the control sequence of the yeast phosphoglycerate kinase (PGK) gene to generate a controllable yeast expression system.

The PGK gene control sequence includes a unique PvuI restriction site which lies upstream of the TATA box (see copending published European patent application EP-0-073-635), and by analogy with control of the CYC1 promoter should allow a1/α2 regulation of the PGK promoter to be exerted.

Figure 4:
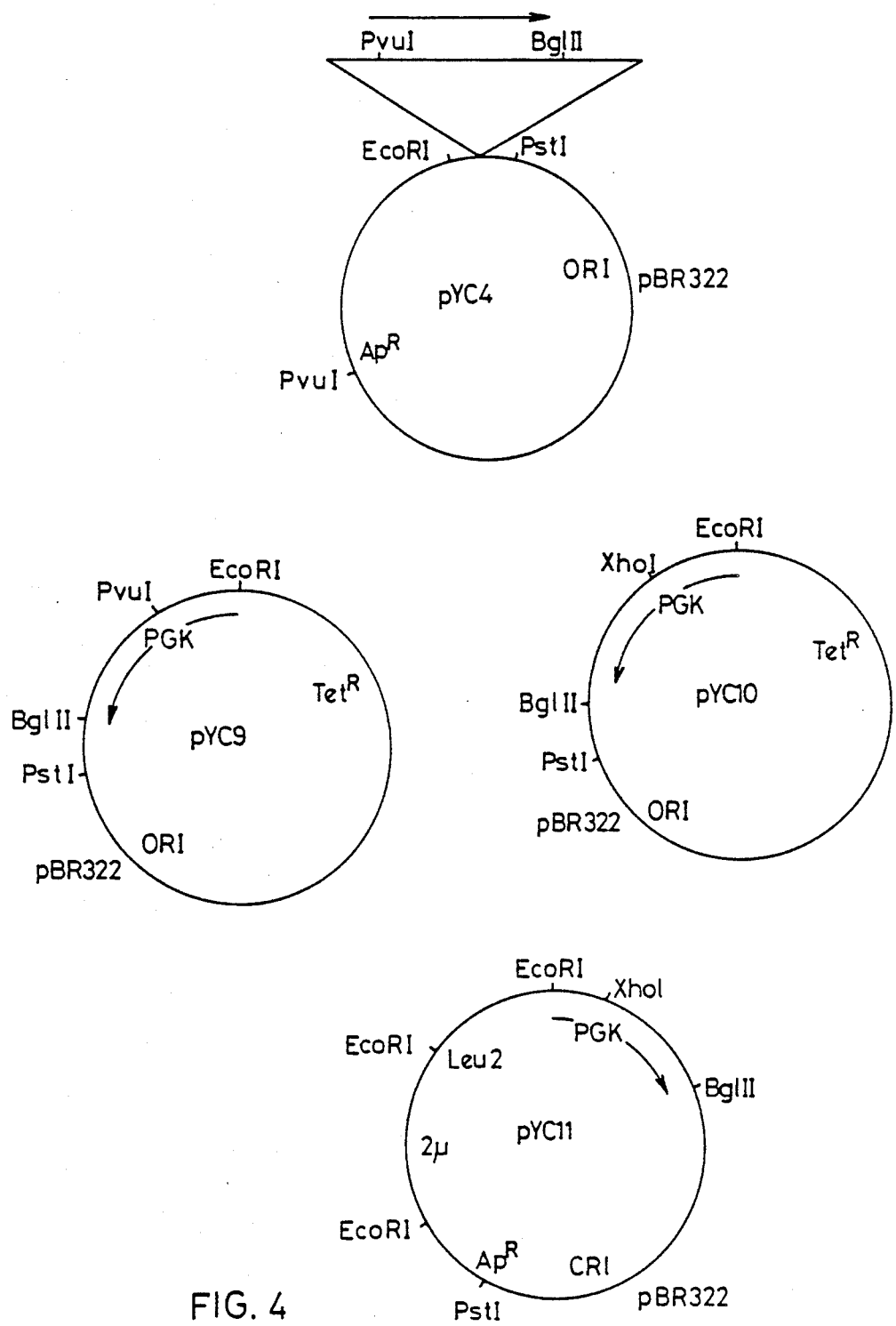
FIG. 4 are maps of plasmids pYC4, pYC9, pYC10 and pYC11.

To generate a plasmid comprising the PGK gene promoter and a unique PvuI site a plasmid, pYC9, was constructed (FIG. 4). The PGK gene promoter sequence for construction of pYC9 was obtained from plasmid pYC4. Plasmid pYC4 was constructed by digesting pMA 3013 (5 μg) (European Patent Application EP-A2-0073635-pMA 3013 has now been renumbered as pMA 91) with Hind III (10 units) in buffer containing 7 mM Tris. HCl pH 7.4, 7 mM MgCl$_2$ and 60 mM NaCl for 1 hour at 37° C. The DNA fragments were separated on a 0.7% Agarose gel and the Hind III fragment carrying the PGK promoter and transcriptional terminato was isolated. This fragment was incubated with T4 DNA polymerase and all four deoxynucleotide triphosphates to give a blunt ended DNA fragment (as described in previous Examples). The resultant blunt ended fragment was ligated into pSP 65 (2 μg) (obtained from P & S Biochemicals Ltd.) digested with Hinc II (4 units) in buffer containing 10 mM Tris. HCl pH 7.5, 7 mM $MgCl_2$, 60 mM NaCl, 1 mM dithiothreitol, at 37° C. for 1 hour. The ligation mixture was transformed into E. coli and ampicillin resistant transformants selected. One of these transformants was pYC4.

Plasmid pYC4 (2 μg) was digested with PstI (4 units) in 20 mM Tris. HCl pH 7.5, 10 mM $MgCl_2$, 1 mM dithiothreitol and 50 mM NaCl at 37° C. for 1 hour, and then the mixture was made up to 100 mM Tris.HCl pH 7.5 and 5 units of EcoRI was added. Incubation at 37° C. was continued for a further hour. The DNA fragments generated were separated by electrophoresis on a 0.7% agarose gel in TAE buffer. The smallest fragment carried the PGK promoter and transcriptional terminator, and was isolated from the gel by the method of Vogelstein & Gillespie (Proc. Natl. Acad. Sci. U.S.A. (1979) 615). Plasmid pBR322 was digested with PstI and EcoRI, as described for pYC4, and the largest DNA fragment isolated from a 0.7% agaroe gel. These two fragments were mixed together at a concentration of 10 μg/ml and ligated together under standard conditions, as described above. The ligation mixture was used to transform E. coli and tetracycline resistant transformants were selected. One isolate, pYC9 was analysed by restriction analysis and used in further studies.

Plasmid pYC9 (5 μg) was digested with PvuI (10 units) in buffer containing 6 mM Tris.HCl pH 7.4, 6 mM $MgCl_2$ 2 mM dithiothreitol, and 150 mM NaCl, at 37° C. for 1 hour. The reaction mixture was extracted with phenol and chloroform as previously described, and ethanol precipitated. The DNA precipitate was collected by centrifugation in an Eppendorf bench centrifuge, air dried and resuspended in 10 μl of water. The single stranded 3' overhangs were removed by treatment with T4 DNA polymerase in the presence of all four deoxynucleoside triphosphates (Maniatis, Fritsch and Sambrook, "Molecular Cloning", Cold Spring Harbor Laboratory (1982). The blunt ended linear molecule was then purified by 0.7% agarose gel electrophoresis and treated with calf intestinal alkaline phosphatase, as described hereinbefore.

The linear, phosphatase treated, blunt ended DNA fragment (12 μg/ml) was ligated to polynucleotide kinase-treated XhoI linker (0.4 μg/ml) [ACCTCGAGGT] under standard conditions. The XhoI linker was synthesised by an automated DNA synthesiser (Patel, Millican, Bose, Titmas, Mock and Eaton (Nucl. Acids. Res. (1982), 10 5605) and was kinase treated as described hereinbefore.

The ligation mixture was transformed into E. coli and tetracycline resistant colonies were selected. Plasmid DNA preparations were made from several transformants (Ish Horowitz and Burke, Nucl. Acids. Res. (1981) 9, 2989) and digested with XhoI as described above. One isolate, pYC10 was used for further studies (FIG. 4).

Plasmid pYC10 (5 μg) was digested in XhoI digestion buffer containing 10 units of enzyme at 37° C. for 1 hour. 5 units of calf intestinal phosphatase was then added and incubation continued for a further 1 hour.

The reaction mixture was then phenol and chloroform extracted and the DNA precipitated, as described hereinbefore. The final precipitate was suspended in 20 μl of TE buffer. The phosphatase treated DNA (12 ug/ml) was ligated to al/α2 repressor sequence oligonucleotides pairs N5 and N6, and N7 and N8 as described hereinbefore, and the ligation mixture was used to transform E. coli. Tetracycline resistant transformants were selected and analysed as described in Example 4, for the presence of cloned oligonucleotides and their orientation.

To generate a yeast expression vector with an al/α2 controllable PGK promoter, plasmid pYC10 (5 μg) comprising an al/α2 repressor sequence cloned into the XhoI site as described above, is digested with BglII (10 units) and EcoRI (10 units) under standard conditions and the smallest DNA fragment isolated from a 1% agarose gel in TAE buffer. Plasmid pMA3013 (5 μg) (European Patent EP-A2-0073635) is digested with BglII (10 units) and partially with EcoRI (5 units) under standard buffer conditions, and the EcorI-BglII fragment comprising the 2μ origin of replication, Leu2 selectable marker, pBR322 origin and ampicillin resistance marker is purified by agarose gel electrophoresis. The two pure DNA fragments are ligated together to generate a plasmid with an al/α2 controllable PGK promoter, a unique BglII expression site, 2μ origin or replication, Leu2 selectable yeast marker, pBR322 origin of replication and an ampicillin resistance E. coli selectable marker (pYC11).

EXAMPLE 10

CONSTRUCTION OF A YEAST EXPRESSION VECTOR WITH A PGK GENE PROMOTER UNDER α2 CONTROL

Plasmid pYC10 digested with XhoI and treated with calf intestinal alkaline phosphatase was used for the insertion of an α2 controllable repressor operator sequence. Annealed- and polynucleotide kinase-treated oligonucleotides N9–12 were ligated to XhoI cut and phosphatase treated pYC10 as described for oligionucleotide insertions in the previous examples. The ligation mixture was transformed into E. coli and tetracycline resistant transformants obtained. These were analysed and insert orientation determined, as described previously. Those plasmids comprising inserts are used to generate an expression plasmid identical to pYC11, except that the PGK gene promoter is regulated by α2 protein, using the same protocol as described in Example 9.

EXAMPLE 11

CONTROLLED EXPRESSION OF HETEROLOGOUS STRUCTURAL GENES IN YEAST USING CONTROLLABLE REPRESSOR OPERATOR SEQUENCES

Yeast expression vectors carrying a strong promoter such as the PGK gene promoter and an inserted al/α2 or α2 controllable repressor operator sequence can be used in conjunction with a yeast strain carrying a conditional mutation in the α2 repressor gene, to give a controllable expression system. For example, a vector of the type pYC11 described in FIG. 4, with a unique BglII restriction site for insertion of a heterologous structural gene between the promoter sequences and transcriptional terminator, can be used to express a foreign gene e.g. methionine-prochymosin (Mellor, Dobson, Roberts, Tuite, Emtage, White, Lowe, Kingsman, Kingsman and Patel, Gene (1983) 24 1). Due to the presence of the al/α2 or α2 controllable repressor sequences, transcription from the promoter is dependent upon the activity of the repressor protein. In a yeast strain carrying a temperature sensitive mutation in either the al or α2 repressor gene, such that at the permissive temperature (e.g. below 36° C.), the α2 protein is functional, but at the restrictive temperature (above 36° C.) it is inactive, transcription of the heterologous structural gene will proceed only at the restrictive temperature.

In the production of foreign proteins in yeast using this expression system, cells are grown to high biomass at the permissive temperature and a shift to the non-permissive temperature allows heterologous polypeptide accumulation.

Temperature-sensitive (ts) mutations in either al or α2 can be selected and screened using a yeast diploid strain carrying a selectable marker gene which is uner al/α2 control and one other auxotrophic marker gene which is under al/α2 control. An example of such a yeast diploid strain is strain F100 which has the following genotype.

MATαHO::TRP1, trp1-1, Leu 2-3,-112, ura 3, ade 2-1, his 3-11,15

MATαHO::LACZ, trp1-1, leu 2-3,-112, ura 3, ade 2-1, his 4

Strain F100 was obtained by mating of the yeast haploid strains K1114 and K757. Strain K757 is a standard yeast strain prepared by replacing the BglII-BglII fragment of the HO gene with the EcoRI-BglII fragment of the yeast TRP1 gene. The HO-β Galactosidase construction of strain K1114 was made by inserting the Lac Z SalI fragment from pMC 1871 into a Xho linker mutant of the HO gene to produce a yeast strain carrying a copy of the LACZ gene fused to the promoter of the homothallism (HO) gene. The resultant strain is similar to one described by Jensen (Jensen R., PhD Thesis, University of Oregon, 1983). It will be appreciated, however, that the above yeast strains are purely exemplary and other yeast strains which have appropriate marker genes under al/α2 control may be used.

Strain F100 carries a copy of the TRP1 gene and the LACZ gene each fused to the promoter of the homothallism (HO) gene and thus should be under al/α2 control. Both these genes are expressed (i.e. non-repressed) in either haploid strains or in diploids which carry deletions in either MATa or MATα, whilst in the diploid, F100, both genes are repressed (i.e. have a trp−, lac− phenotype) suggesting that they are under al/α2 control.

To isolate ts mutations, F100 is mutagenisised with ethylmethane sulfonate (EMS) to 5-25% survival according to the procedure of Fink, G. C. (Methods of Enzymology (1970) XVII A p. 59-78) and plated out onto nitrocellulose filters placed on minimal medium (6.7 gl$^{-1}$ Yeast Nitrogen Base (Difco), w/o amino acids, 20 gl$^{-1}$ agar, 20 gl$^{-1}$ glucose) supplemented for all auxotrophic requirements with the exception of tryptophan. The plates are incubated at the restrictive temperature (for example 36° C. for 3-4 days). Mutants which are defective in either al or α2 should no longer repress transcription at the HO::TRP1 gene and thus should be able to grow in absence of tryptophan. To check that the mutations are trans acting (i.e. no longer repressed at the HO::LacZ gene) the colonies are screened for β-galactosidase activity in the following way. The nitrocellulose filters containing trp+ colonies are placed in liquid nitrogen for 1-5 minutes and each subsequently transferred to Whatman No. 1, 9.0 cm filters soked in 1.75 ml Z buffer containing 25 μg/ml of 5-bromo-4-chloro-3-indolyl-β-D-galactopyranoside (X-gal).

The filters, sealed in petri dishes, are incubated at 30° C. for 1-6 hours to allow LAC+ colonies to turn blue. Colonies which have β-galactosidase activity are rescued from the nitrocellulose filters by plating out onto YEPD (10 gl$^{-1}$ Yeast Extract 20 gl$^{-1}$ Bactopeptone, 20 gl$^{-1}$ agar, 20 gl$^{-1}$ glucose) agar plates.

To check for temperature-sensitive phenotype, mutants are grown at both the permissive (23° C.) and restrictive temperature in the absence or presence of tryptophan and screened for β-galactosidase activity using the methods described above. Mutants which are ts for repression at both HO promoters are presumed to carry ts mutations in either al or α2. To determine this, the mutants are transformed with a yeast/E. coli shuttle vector containing either the wild-type al or α2 genes and tested for complementation of the mutant phenotype at the restrictive temperature.

The selection and screening protocol described above may select only for mutations in the α2 gene that affect the combined action of al/α2 repression of transcription initiated from a promoter harbouring the al/α2 operator sequence(s). Thus any ts α2 mutation isolated by this method may not affect the specific action of α2 repressor on α2 operator sequences.

To isolate ts mutations that specifically affect this action, a modification of the screening protocol in the previous section can be used.

A haploid yeast strain carrying an auxotrophic marker which is under al/α2 control may be used. An example of such a yeast strain is strain K 757, discussed above which has the following genotype: MATα, HO::TRP1, trp1, can 1-100, leu 2-3,-112, his 3-11,15, ade 2-1 ura3,is transformed with a yeast/E. coli vector carrying the CYC1/LACZ gene fusion e.g. pLG312 (Guarente, L et al PNAS USA (1982), 79, 7410-7414) and harbouring an α2 operator sequence between the Upstream Activator Sequence (UAS) and TATA of the CYC1 promoter (as previously described in Example 1).

The 757 strain transformed with the above plasmid is mutagenesised as described previously and plated out onto nitrocellulose filters on YEPD agar medium and incubated at the restrictive temperature (e.g. 36° C.). Colonies that turn blue using the method described in the previous section are presumed to be defective in α2 at the restrictive temperature. Mutants are further tested for temperature-sensitivity by their ability to repress transcription from the CYC1 promoter at the permissive temperature (23° C.). Complementation analysis with a Yeast/E. coli plasmid containing the wild-type MATα gene should confirm whether the mutation is specific for the α2 gene.

EXAMPLE 12

USE OF THE α2 CONTROLLABLE REPRESSOR SEQUENCE IN HIGHER EUKARYOTIC CELLS

Figure 5:
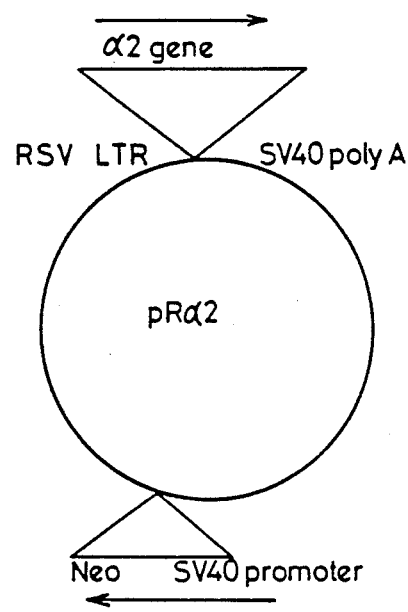
FIG. 5 is a map of plasmid pRα2, a plasmid for the expression of the α2 gene in mammalian cells.

To demonstrate that the α2 control system functions in higher eukaryotic cells it is first necessary to construct eukaryotic expression vectors which direct the synthesis of the α2 repressor protein. For instance, a structural gene coding for the α2 repressor protein is inserted into a unique cloning site between the Rous Sarcoma Virus Long Terminal Repeat and Simian Virus 40 (SV40) polyadenylation site of an appropriate expression plasmid to provide a plasmid such as p Rα2 (FIG. 5). This plasmid additionally carries a neomycin resistance gene (neo) under the control of the SV40 early promoter to permit antibiotic selection of transfected cell lines. Plasmid pRα2 is transfected into an appropriate mammalian cell line, e.g. mouse L cells, and G418 resistant clones which express the α2 repressor protein are obtained.

The α2 protein expressing clones obtained above are then transfected with a plasmid expressing an easily assayable gene product, such as chloramphenicol acetyl transferase (CAT) which expression is under α2 control. In this latter plasmid the expression of the CAT gene is under the control of a promoter known to function in the host cells, e.g. the SV40 early promoter, and one or more copies of the α2 controllable repressor sequence are inserted into the promoter sequence. The levels of CAT expressed by the transfected cells are monitored i.e. by monitoring CAT activity, and reflect the transcriptional control exerted by the α2 protein. In the first instance the α2 repressor sequence is inserted adjacent to the 72 base pair repeats of the SV40 early promoter.

Vectors expessing the al/α2 genes can be produced in a similar manner.

It will, of course, be understood that the present invention has been described above purely by way of example, and modifications of detail can be made within the scope and spirit of the invention.

I claim:

1. A eukaryotic expression vector comprising an expression control sequence including a functional eukaryotic promoter not normally under mating type control and a heterologous structural gene located relative to the expression control sequence such that the expression control sequence is capable of directing expression of the heterologous structural gene, wherein the expression control sequence includes a controllable repressor operator sequence comprising a DNA sequence which is capable of repressing expression in the presence of a gene product or a combination of gene products of the yeast mating type loci.

2. A eukaryotic expression vector according to claim 1 wherein the controllable repressor operator sequence comprises a DNA sequence which is capable of repressing expression in the presence of a combination of the al and α2 gene products of MATαand MATa yeast mating type locus alleles.

3. A eukaryotic expression vector according to claim 1 wherein the controllable repressor operator sequence comprises a DNA sequence which is capable of repressing expression in the presence of the α2 gene product of the MATα yeast mating type locus allele.

4. A eukaryotic host organism transformed with an expression vector according to claim 1.

5. A eukaryotic host organism according to claim 4 wherein the host organism is further transformed with a second eukaryotic expression vector capable of providing a controllable source of either a combination of the al and α2 gene products of the MATa and MATα yeast mating type alleles or the α2 gene product of the MATα yeast mating type allele.

6. A eukaryotic host organism according to claim 4 wherein the host organism is a yeast.

7. A controllable repressor operator sequence capable, when inserted into the expression control sequence of a eukaryotic expression vector, of repressing expression in the presence of a combination of the al and α2 gene products of the MATa and MATα yeast mating type allele.

8. A controllable repressor operator sequence capable, when inserted into the expression control sequence of a eukaryotic expression vector, of repressing expression in the presence of the α2 gene product of the MATα yeast mating type locus.

9. A method of preparing a polypeptide comprising culturing a eukaryotic host organism transformed with a vector according to claim 1 in the presence of one or more gene products of the yeast mating type locus capable of repressing expression of the heterologous structural gene coding for the polypeptide, until a predetermined cell density has been established, and subsequently reducing the level of the gene product or products of the yeast mating type locus, thereby allowing expression of the heterologous structural gene and production of the polypeptide.

10. A eukaryotic expression vector comprising an expression control sequence including a functional yeast promoter not normally under mating type control and a restriction site suitable for the insertion of a heterologous gene located relative to the expression control sequence such that the expression control sequence is capable of directing expression of a heterologous structural gene to be inserted at said restriction site, wherein the expression control sequence includes a controllable repressor operator sequence comprising a DNA sequence which is capable of repressing expression in the presence of a gene product or a combination of gene products of the yeast mating type loci.

11. A eukaryotic host organism transformed with an expression vector according to claim 2.

12. A eukaryotic host organism transformed with an expression vector according to claim 3.

13. A eukaryotic host organism according to claim 11 wherein the host organism is further transformed with a second eukaryotic expression vector capable of providing a controllable source of either a combination of the al and α2 gene products of the MATa and MATα yeast mating type alleles or the α2 gene product of the MATα yeast mating type allele.

14. A eukaryotic host organism according to claim 12 wherein the host organism is further transformed with a second eukaryotic expression vector capable of providing a controllable source of either a combination of the al and α2 gene products of the MATa and MATα yeast mating type alleles or the α2 gene product of the MATα yeast mating type allele.

15. A eukaryotic host organism according to claim 11 wherein the host organism is a yeast.

16. A eukaryotic host organism according to claim 12 wherein the host organism is a yeast.

17. A eukaryotic host organism according to claim 5 wherein the host organism is a yeast.

18. A eukaryotic host organism according to claim 13 wherein the host organism is a yeast.

19. A eukaryotic host organism according to claim 14 wherein the host organism is a yeast.

20. A eukaryotic expression vector according to claim 2 wherein said DNA sequence comprises a double stranded sequence of about twenty base pairs having subsequences of about seven base pairs at opposite ends and in complementary strands of the sequence, wherein the subsequences are substantially inverted repeats each of the other.

21. A eukaryotic expression vector according to claim 2 wherein said DNA sequence is selected from the group consisting essentially of the following DNA sequences:

CAATGTAGAAAAGTACATCA,

GCTTGTTAATTTACACATCA,

TCATGTACTTTTCTGCATCA,

CCGCGTTAAAACCTACATCA,

TTATGTTAAAAGTTACATCC,

GCCTGCGATGAGATACATCA,

TAGAGTGAAAAAGCACATCG,

TCATGTATTCATTCACATCA,

ACATGTCTTCAACTGCATCA,

TCGTGTATTTACTTACATCA,

TCATGTTATTATTTACATCA,

TCATGTCCACATTAACATCA and

GCGTTTACAACGCTTCATCA.

22. A eukaryotic expression vector according to claim 2 wherein said DNA sequence has substantially the following nucleotide base sequence:

TC(A of G)TGTNN(A or T)NANNTACATCA wherein N denotes a nucleotide base selected from adenine, thymine, guanine and cytosine.

23. A eukaryotic expression vector according to claim 3 wherein said DNA sequence comprises a double stranded sequence of about thirty-three base pairs having subsequences of about ten base pairs at opposite ends and in complementary strands of the sequence, wherein the subsequences are substantially inverted repeats each of the other.

24. A eukaryotic expression vector according to claim 3 wherein said DNA sequence is selected from the group consisting essentially of the following DNA sequences:

GTGTGTAATTACCCAAAAAGGAAATT-TACATGT,

GCATGTAATTACCGTAAAAGGAAAT-TACATGG and

TCATGTACTTACCCAATTAGGAAATT-TACATGG.

25. A eukaryotic expression vector according to claim 3 wherein said DNA sequence has substantially the following nucleotide base sequence:

GCATGTAATTACCCAAAAAGGAAATT-TACATGG.

26. A controllable repressor operator sequence according to claim 7 wherein said sequence comprises a double-stranded DNA sequence of about twenty base pairs at opposite ends and in complementary strands of the sequence, wherein the subsequences are substantially inverted repeats each of the other.

27. A controllable repressor operator sequence according to claim 7 wherein said sequence is selected from the group consisting essentially of the following DNA sequences:

CAATGTAGAAAAGTACATCA,

GCTTGTTAATTTACACATCA,

TCATGTACTTTTCTGCATCA,

CCGCGTTAAAACCTACATCA,

TTATGTTAAAAGTTACATCC,

GCCTGCGATGAGATACATCA,

TAGAGTGAAAAAGCACATCG,

TCATGTATTCATTCACATCA,

ACATGTCTTCAACTGCATCA,

TCGTGTATTTACTTACATCA,

TCATGTTATTATTTACATCA,

TCATGTCCACATTAACATCA and

GCGTTTAGAACGCTTCATCA.

28. A controllable repressor operator sequence according to claim 7 wherein said sequence has substantially the following nucleotide base sequence:

TC(A or G)TGTNN(A or T)NANNTACATCA wherein N denotes a nucleotide base selected from adenine, thymine, guanine and cytosine.

29. A controllable repressor operator sequence according to claim 8 wherein said sequence comprises a double-stranded DNA sequence of about thirty-three base pairs having subsequences of about ten base pairs at opposite ends and in complementary strands of the sequence, wherein the subsequences are substantially inverted repeats each of the other.

30. A controllable repressor operator sequence according to claim 8 wherein said sequence is selected from the group consisting essentially of the following DNA sequences:

GTGTGTAATTACCCAAAAAGGAAATT-TACATGT,

GCATGTAATTACCGTAAAAGGAAAT-TACATGG and

TCATGTACTTACCCAATTAGGAAATT-TACATGG.

31. A controllable repressor operator sequence according to claim 8 wherein said sequence has substantially the following nucleotide base sequence:

GCATGTAATTACCCAAAAAGGAAATT-TACATGG.

32. A yeast expression vector comprising an expression control sequence including a functional yeast promoter not normally under mating type control and a heterologous structural gene located relative to the expression control sequence such that the expression control sequence is capable of directing expression of the heterologous structural gene, wherein the expression control sequence includes a controllable repressor operator sequence comprising a DNA sequence which is capable of repressing expression in the presence of a gene product or a combination of gene products of the yeast mating type loci.

33. The yeast expression vector according to claim 32, wherein the controllable repressor operator sequence comprises a DNA sequence which is capable of repressing expression in the presence of a combination of the a1 and α2 gene products of MATα and MATa yeast mating type locus alleles.

34. The yeast expression vector according to claim 32, wherein the controllable repressor operator sequence comprises a DNA sequence which is capable of repressing expression in the presence of α2 gene product of the MATα yeast mating type locus allele.

35. A yeast host organism transformed with an expression vector according to claim 32.

36. The yeast host organism according to claim 35, said host organism further transformed with a second yeast expression vector capable of providing a controllable source of either a combination of the a1 and α2 gene products of the MATa and MATα yeast mating type alleles or the α2 gene product of the MATα yeast mating type allele.

37. A controllable repressor operator sequence capable, when inserted into the expression control sequence of a yeast expression vector, of repressing expression in the presence of a combination of the a1 and α2 gene products of the MATa and MATα yeast mating type allele.

38. A controllable repressor operator sequence capable, when inserted into the expression control sequence of a yeast expression vector, of repressing expression in the presence of the α2 gene product of the MATα yeast mating type locus.

39. A method for preparing a polypeptide comprising culturing a yeast host organism transformed with a vector according to claim 32 in the presence of at least one gene product of the yeast mating type locus capable of repressing expression of the heterologous stuctural gene coding for the polypeptide, until a predetermined cell density has been established, and subsequently reducing the level of the at least one gene product of the yeast mating type locus, allowing expression of the heterologous structural gene and production of the polypeptide.

40. A yeast expression vector comprising an expression control sequence including a functional yeast promoter not normally under mating type control and a restriction site adapted for the insertion of a heterologous gene located relative to the expression control sequence such that the expression control sequence is capable of directing expression of a heterologous structural gene to be inserted at said restriction site, wherein the expression control sequence includes a controllable repressor operator sequence comprising a DNA sequence which is capable of repressing expression in the presence of a gene product or a combination of gene products of the yeast mating type loci.

41. A yeast host organism transformed with an expression vector according to claim 33.

42. A yeast host organism transformed with an expression vector according to claim 34.

43. The yeast host organism according to claim 41, wherein the host organism is further transformed with a second yeast expression vector capable of providing a controllable source of either a combination of the a1 and α2 gene products of the MATa and MATα yeast mating type alleles or the α2 gene product of the MATα yeast mating type allele.

44. The yeast host organism according to claim 42, wherein the host organism is further transformed with a second yeast expression vector capable of providing a controllable source of either a combination of the a1 and α2 gene products of the MATa and MATα yeast mating type alleles or the α2 gene product of the MATα yeast mating type allele.

45. The yeast expression vector according to claim 33, wherein said DNA sequence comprises a double stranded sequence of about twenty base pairs having subsequences of about seven base pairs at opposite ends and in complementary strands of the sequence, wherein the subsequences are substantially inverted repeats each of the other.

46. A yeast expression vector according to claim 33, wherein said DNA sequence is selected from the group consisting essentially of the following DNA sequences:

CAATGTAGAAAAGTACATA,

GCTTGTTAATTTACACATCA,

TCAGTACTTTTCTGCATCA,

CCGCGTTAAAACCTACATCA,

TTATGTTAAAAGTTACATCC,

GCCTGCGATGAGATACATCA,

TAGAGTGAAAAAGCACATCG,

TCATGTATTCATTCACATCA,

ACATGTCTTCAACTGCATCA,

TCGTGTATTTACTTACATCA,

TCATGTTATTATTTACATCA,

TCATGTCCACATTAACATCA, and

GCGTTTAGAACGCTTCATCA.

47. A yeast expression vector according to claim 33, wherein said DNA sequence has substantially the following nucleotide base sequence:

TC(A or G)TGTNN(A or T)NANNTACATCA wherein N denotes a nucleotide base selected from adenine, thymine, guanine and cytosine.

48. A yeast expression vector according to claim 34, wherein said DNA sequence comprises a double stranded sequence of about thirty-three base pairs having subsequences of about ten base pairs at opposite ends and in complementary strands of the sequence, wherein the subsequences are substantially inverted repeats each of the other.

49. A yeast expression vector according to claim 34, wherein said DNA sequence is selected from the group consisting essentially of the following DNA sequences:

GTGTGTAATTACCCAAAAAGGAAATT-TACATCT,

GCATGTAATTACCGTAAAAGGAAAT-TACATGG and

TCATGTACTTACCCAATTAGGAAATT-TACATGG.

50. A yeast expression vector according to claim 34, wherein said DNA sequence has substantially the following nucleotide base sequence:

GCATGTAATTACCCAAAAAGGAAATT-TACATGG.

51. A controllable repressor operator sequence according to claim 37, wherein said sequence comprises a double-stranded DNA sequence of about twenty base pairs at opposite ends and in complementary strands of the sequence, wherein the subsequences are substantially inverted repeats each of the other.

52. A controllable repressor operator sequence according to claim 37, wherein said sequence is selected from the group consisting essentially of the following DNA sequences:

CAATGTAGAAAAGTACATCA,

GCTTGTTAATTTACACATCA,

TCATGTACTTTTCTGCATCA,

CCGCGTTAAAACCTACATCA,

TTATGTTAAAAGTTACATCC,

GCCTGCGATGAGATACATCA,

TAGAGTGAAAAAGCACATCG,

TCATGTATTCATTCACATCA,

ACATGTCTTCAACTGCATCA,

TCGTGTATTTACTTACATCA,

TCATGTTATTATTTACATCA,

TCATGTCCACATTAACATCA, and

GCGTTTAGAACGCTTCATCA.

53. A controllable repressor operator sequence according to claim 37, wherein said sequence has substantially the following nucleotide base sequence:

TC(A or G)TGTNN(A or T)NANNTACATCA wherein N denotes a nucleotide base selected from adenine, thymine, guanine and cytosine.

54. A controllable repressor operator sequence according to claim 38, wherein said sequence comprises a double-stranded DNA sequence of about thirty-three base pairs having subsequences of about ten base pairs at opposite ends and in complementary strands of the sequence, wherein the subsequence are substantially inverted repeats each of the other.

55. A controllable repressor operator sequence according to claim 38, wherein said sequence is selected from the group consisting essentially of the following DNA sequences:

GTGTGTAATTACCCAAAAAGGAAATT-TACATGT,

GCATGTAATTACCGTAAAAGGAAAT-TACATGG, and

TCATGTACTTACCCAATTAGGAAATT-TACATGG.

56. A controllable repressor operator sequence according to claim 38, wherein said sequence has substantially the following nucleotide base sequence:

GCATGTAATTACCCAAAAAGGAAATT-TACATGG.

* * * * *